United States Patent
Asahara et al.

(10) Patent No.: US 7,211,416 B2
(45) Date of Patent: May 1, 2007

(54) METHOD FOR PRODUCING L-LYSINE USING METHANOL-UTILIZING BACTERIUM

(75) Inventors: Takayuki Asahara, Kawasaki (JP); Seiko Hirano, Kawasaki (JP); Hisashi Yasueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 458 days.

(21) Appl. No.: 10/760,283

(22) Filed: Jan. 21, 2004

(65) Prior Publication Data

US 2004/0214296 A1 Oct. 28, 2004

(30) Foreign Application Priority Data

Jan. 29, 2003 (JP) ............................. 2003-020513

(51) Int. Cl.
C12P 13/14 (2006.01)
(52) U.S. Cl. .................................... 435/115
(58) Field of Classification Search ................. 435/115
See application file for complete search history.

(56) References Cited

U.S. PATENT DOCUMENTS

| | | | |
|---|---|---|---|
| 3,907,637 A | 9/1975 | Nakayama et al. | 195/29 |
| 3,907,641 A | 9/1975 | Nakayama et al. | 195/49 |
| 5,217,883 A | 6/1993 | Anazawa et al. | 435/252.3 |
| 6,261,825 B1* | 7/2001 | Hanson et al. | 435/252.5 |
| 6,461,852 B1 | 10/2002 | Tsujimoto et al. | |
| 2003/0013174 A1 | 1/2003 | Tsujimoto et al. | |
| 2003/0049805 A1 | 3/2003 | Nagase et al. | |
| 2003/0124687 A1 | 7/2003 | Gunji et al. | |
| 2003/0166174 A1 | 9/2003 | Ono et al. | |
| 2003/0232338 A1 | 12/2003 | Usuda et al. | |
| 2004/0142435 A1 | 7/2004 | Gunji et al. | |
| 2004/0146974 A1 | 7/2004 | Gunji et al. | |
| 2004/0166570 A1 | 8/2004 | Yasueda et al. | |
| 2004/0170985 A1 | 9/2004 | Usuda et al. | |
| 2004/0170986 A1 | 9/2004 | Usuda et al. | |
| 2004/0170987 A1 | 9/2004 | Usuda et al. | |
| 2004/0171134 A1 | 9/2004 | Yasueda et al. | |
| 2004/0191875 A1 | 9/2004 | Takeshita et al. | |
| 2004/0214296 A1 | 10/2004 | Asahara et al. | |
| 2004/0229311 A1 | 11/2004 | Hirano et al. | |

FOREIGN PATENT DOCUMENTS

| | | |
|---|---|---|
| EP | 0733710 | 9/1996 |
| EP | 1188822 | 3/2002 |
| EP | 1 266 966 A | 12/2002 |
| JP | 45-25273 | 8/1970 |
| JP | 50-25790 | 3/1975 |
| JP | 52-18886 | 2/1977 |
| WO | WO90/12105 | 10/1990 |

OTHER PUBLICATIONS

Hiroshi Aida et al., Amino Acid Fermentation, Kabushiki Kaisha Gakukai Shuppan Center, May 30, 1986, p. 273-305.
A. T. Moore et al., Genetic Mapping in *Methylophilus methylotrophus* AS1, Journal of General Microbiology, 1983, p. 785-799, vol. 129.
Mary L. O'Connor et al., Linkage Relationships Between Mutants of *Methylobacterium organophilum* Impaired in their Ability to Grow on One-carbon Compounds, Journal of General Microbiology, 1978, p. 105-111, vol. 104.
J. D. Windass, Improved conversion of methanol to single-cell protein by *Methylophilus methylotrophus*, Nature, 1980, p. 396-401, vol. 287.
C. S. Kim et al., Creating auxotrophic mutants in *Methylophilus methylotrophus* AS1 by combining electroporation and chemical mutagenesis, Appl. Microbiol. Biotechnol., 1997, p. 105-108, vol. 48.
Shin-ichi Matsuyama et al., Construction and Characterization of a Deletion Mutant Lacking *micF*, a Proposed Regulatory Gene of OmpF Synthesis in *Escherichia coli*, Journal of Bacteriology, Jun. 1985, p. 1196-1202, vol. 162, No. 3.
U.S. Appl. No. 10/716,470, filed Nov. 20, 2003, Gunji et al.
U.S. Appl. No. 09/926,299, filed Oct. 9, 2001, Gunji et al.
U.S. Appl. No. 10/791,853, filed Mar. 4, 2004, Takeshita et al.
Motoyama, H., et al., "Overproduction of L-Lysine from Methanol by *Methylobacillus glycogenes* Derivatives Carrying a Plasmid with a Mutated *dapA* Gene", Applied and Environmental Microbiology, 2001, vol. 67, No. 7, p. 3064-3070.
Lee, G.H., "Lysine Production from Methanol at 50° C. Using *Bacillus methanolicus*: Modeling Volume Control, Lysine Concentration, and Productivity Using a Three-Phase Continuous Simulation", Biotechnology and Bioengineering, 1996, vol. 49, p. 639-653.

(Continued)

*Primary Examiner*—Herbert J. Lilling
(74) *Attorney, Agent, or Firm*—Cermak & Kenealy, LLP; Shelly Guest Cermak

(57) ABSTRACT

L-Lysine is produced by culturing a methanol-utilizing bacterium which requires L-methionine for its growth and has an ability to produce L-lysine in a medium containing methanol as a main carbon source to produce and accumulate L-lysine in culture and collecting the L-lysine from the culture.

4 Claims, No Drawings

OTHER PUBLICATIONS

Tani, Y., et al., "Production of L-Serine by a Methanol-utilizing Bacterium, *Arthrobacter globiforms* SK-200", Agric. Biol. Chem., 1978, vol. 42, No. 12, p. 2275-2279.

Gunji, Y., et al., "Characterization of the L-Lysine Biosynthetic Pathway in the Obligate Methlotroph *Methylophilus methylotrophus*", Biosci. Biotechnol. Biochem., 2004, vol. 68, No. 7, 1449-1460.

Search Report, Oct. 22, 2004, French Intellectual Property Office.

* cited by examiner

METHOD FOR PRODUCING L-LYSINE USING METHANOL-UTILIZING BACTERIUM

BACKGROUND OF THE INVENTION

1. Field of the Invention

The present invention relates to a technique useful in the microbial industry. More specifically, the present invention relates to a method for producing L-lysine by fermentation.

2. Brief Description of the Related Art

L-Lysine is produced by fermentation using microorganisms that belong to the genus *Corynebacterium, Bacillus, Escherichia* or the like (see "Amino Acid Fermentation", Ed. By H. Aida et al., the Japan Scientific Societies Press [Gakkai Shuppan Center], 1st Edition, published on May 30, 1986). Bacterial strains isolated from nature or mutant strains thereof auxotrophic in nutrients have been used to improve the production in these microorganisms. Furthermore, various techniques have been disclosed for increasing the L-lysine-producing ability using recombinant DNA techniques to enhance L-lysine biosynthetic enzymes (WO95/16042).

Productivity of L-lysine has been considerably increased by breeding of microorganisms such as those mentioned above as well as improvements of production methods. However, in order to respond to the increase in future demands, the development of a method which provides more efficient production of L-lysine at a lower cost is clearly necessary, and therefore, still represents a need in the art.

Methanol is a fermentation raw material which is available in large amounts at a low cost. Methods for producing L-amino acids by fermentation using methanol are known, and include methods using microorganisms that belong to the genus *Achromobacter* or *Pseudomonas* (Japanese Patent Laid-open (Kokai) No. 45-25273), *Protaminobacter* (Japanese Patent Publication (Kokoku) No. 49-125590), *Protaminobacter* or *Methanomonas* (Japanese Patent Laid-open (Kokai) No. 50-25790), *Microcyclus* (Japanese Patent Laid-open (Kokai) No. 52-18886), *Methylobacillus* (Japanese Patent Laid-open (Kokai) No. 4-91793), *Bacillus* (Japanese Patent Laid-open (Kokai) No. 3-505284), *Methylophilus* (WO00/61723) and so forth.

Furthermore, for strict methanol-utilizing bacteria, especially *Methylophilus* bacteria, it has been reported that it is difficult to obtain auxotrophic mutants by the usual methods ((1983), vol. 129, pp. 785–799; M. L. O'Connor and R. S. Hanson, Journal of General Microbiology (1978), vol. 104, pp. 105–111). Therefore, when attempts were made to obtain a glutamine auxotrophic strain, for example, only a strain having temperature-sensitive auxotrophy could be obtained (Windass J. D. et al., Nature, 287, pp. 396–401 (1980)). Even when a special procedure, for example, suspending cells of a bacterial strain in a solution containing a mutagenesis agent for DNA and applying a voltage to the cells to forcibly make holes in the cell membranes and thereby flow the mutagenesis agent into the cells (electroporation) was used, only three kinds of mutant strains, i.e., a folic acid auxotrophic strain, a strain polyauxotrophic in serine and alanine, and a strain polyauxotrophic in glutamic acid and inositol, could be obtained (C. S. Kim and T. K. Wood, Applied Microbiol. & Biotechnology, 48, pp. 105–108 (1997)).

In addition, WO00/61723 also described that *Methylophilus methylotrophus* was subjected to mutagenesis treatment using a chemical mutagenesis agent to obtain a leaky casamino acid auxotrophic strain, and that strain produced valine, leucine and isoleucine. However, judging from the characteristics of the mutant strain, it appears that the strain became a leaky casamino acid auxotrophic strain because the change in cell membranes allowed various amino acids in the medium to permeate the cells.

SUMMARY OF THE INVENTION

An object of the present invention is to provide a method for improving efficiency of L-lysine production utilizing a methanol-utilizing bacterium.

It is a further object of the present invention to provide a method for producing L-lysine comprising culturing a methanol-utilizing bacterium which requires L-methionine for its growth and has an ability to produce L-lysine in a medium containing methanol as a main carbon source, allowing accumulation of L-lysine in a culture, and collecting the L-lysine from the culture.

It is a further object of the present invention to provide the method as described above, wherein the bacterium is a *Methylophilus* bacterium.

It is a further object of the present invention to provide the method as described above, wherein the *Methylophilus* bacterium is *Methylophilus methylotrophus*.

It is a further object of the present invention to provide the method as described above, wherein the *Methylophilus* bacterium is modified so that an enzymatic activity of dihydrodipicolinate synthase and an L-lysine secretion system are enhanced.

It is even a further object of the present invention to provide a *Methylophilus* bacterium which requires L-methionine for its growth and has an ability to produce L-lysine.

It is a further object of the present invention to provide the *Methylophilus* bacterium as described above, which is *Methylophilus methylotrophus*.

It is a further object of the present invention to provide the *Methylophilus* bacterium as described above, which is modified so that an enzymatic activity of dihydrodipicolinate synthase and an L-lysine secretion system are enhanced.

According to the present invention, L-lysine production using methanol-utilizing bacteria can be improved.

DESCRIPTION OF PREFERRED EMBODIMENTS

The inventors of the present invention assiduously studied in order to achieve the aforementioned objects. As a result, they succeeded in imparting methionine auxotrophy to a methanol-utilizing bacterium, and found that this characteristic improved L-lysine productivity from methanol by the methanol-utilizing bacterium.

In the present invention, the "ability to produce L-lysine" means an ability of the bacterium of the present invention to cause accumulation of L-lysine in a medium in a significant amount, for example, 0.1 g/L or more, when it is cultured in the medium, or an ability of the bacterium of the present invention to significantly increase an amount of free L-lysine in the cells per total mass of the proteins in the cells, for example, 1.5 times or more, compared with the original wild-type strain.

Bacterium of the Present Invention

The bacterium of the present invention is a methanol-utilizing bacterium which requires L-methionine for its growth, also called L-methionine auxotrophy, and has an ability to produce L-lysine. In the present invention, the methanol-utilizing bacterium, or methylotroph, means a bacterium which can grow by utilizing methanol as a major carbon source, and in which an ability to produce L-lysine can be imparted or enhanced via L-methionine auxotrophy. Specific examples include *Methylophilus* bacteria such as *Methylophilus methylotrophus* and *Methylobacillus* bacteria such as *Methylobacillus glycogenes* and *Methylobacillus flagellatum*.

Examples of *Methylophilus methylotrophus* include the AS1 strain (NCIMB 10515) and so forth. The *Methylophilus methylotrophus* AS1 strain (NCIMB 10515) is available form the National Collections of Industrial and Marine Bacteria (Address: NCIMB Lts., Torry Research Station, 135, Abbey Road, Aberdeen AB9 8DG, United Kingdom).

Examples of *Methylobacillus glycogenes* include the T-11 strain (NCIMB 11375), ATCC 21276 strain, ATCC 21371 strain, ATR80 strain (described in Appl. Microbiol. Biotechnol., 42, pp. 67–72 (1994)), A513 strain (described in Appl. Microbiol. Biotechnol., 42, pp. 67–72 (1994)) and so forth. The *Methylobacillus glycogenes* NCIMB 11375 strain is available from the National Collections of Industrial and Marine Bacteria (Address: NCIMB Lts., Torry Research Station, 135, Abbey Road, Aberdeen AB9 8DG, United Kingdom). Examples of *Methylobacillus flagellatum* include the KT strain (described in Arch. Microbiol., 149, pp. 441–446 (1988)) and so forth.

The methanol-utilizing bacterium which requires L-methionine for its growth and has an ability to produce L-lysine can be derived using a methanol-utilizing bacterium which does not require L-methionine (non-auxotrophy in L-methionine) as a starting material. Examples of the methanol-utilizing bacterium which does not require L-methionine for its growth include, but are not limited to, wild-type strains of methanol-utilizing bacteria.

In the present invention, the expression "requires L-methionine for its growth" means that, for example, a strain does not grow when it is cultured in SEII medium not containing L-methionine or having a L-methionine content of 0.001 g/L or less at 30 to 37° C. for 2 days, whereas it grows at a rate, measured as increase in mass of cells per unit time, comparable to that of a wild-type, unmodified, or parent strain, or a rate corresponding to 5% or more, preferably 20% or more, of a wild-type, unmodified, or parent strain, when cultured in the same medium containing at least 0.05 g/L or more of L-methionine. Furthermore, when a desired strain (L-methionine auxotrophic strain) cannot form a colony having a diameter of 1 mm or more even after about 100 cells are applied on a typical plate of SEII agar medium not containing L-methionine, and cultured at 37° C. for 2 days, but has an ability to form colonies having a diameter of 1 mm or more on the same medium containing 1 g/L of L-methionine after culture under the same conditions, the strain "requires L-methionine for its growth".

Examples of the method for deriving an L-methionine auxotrophic strain from an L-methionine non-auxotrophic strain include treating an L-methionine non-auxotrophic strain with physical stimulation capable of mutating a gene, such as ultraviolet rays, X-rays and γ-rays, or treating an L-methionine non-auxotrophic strain with a chemical mutagenesis agent such as N-methyl-N'-nitro-N-nitrosoguanidine (NTG), followed by selecting a strain that has become auxotrophic in L-methionine. Among these, a method of using, for example, NTG is preferred. Although it has conventionally been known that it is extremely difficult to obtain a strain of *Methylophilus methylotrophus* auxotrophic for a specific amino acid, the inventors of the present invention found that an L-methionine auxotrophic strain could be obtained even using a chemical mutagenesis agent.

Furthermore, when the metabolic pathway responsible for the L-methionine synthesis is thought to exist for a methanol-utilizing bacterium, and a gene encoding an enzyme in the pathway has been elucidated, a gene disruption method utilizing homologous recombination can be used to directly disrupt the gene and thereby obtain an L-methionine auxotrophic strain. Moreover, it is also possible to impart L-methionine auxotrophy by utilizing a genetic recombination technique to suppress an activity of an enzyme involved in the L-methionine synthesis. For example, in *Methylophilus methylotrophus*, the metA gene shown in SEQ ID NO: 15 is an example of a gene encoding an enzyme which can be disrupted, or the enzymatice activity suppressed. It is thought that this gene codes for homoserine o-acetyltransferase. As described in more detail herein, *Methylophilus methylotrophus* having metA gene disrupted required L-methionine and showed improved L-lysine productivity.

In addition, examples of the enzyme of which functional deficiency results in L-methionine auxotrophy include the enzymes of the metabolic pathway starting from aspartate semialdehyde to L-methionine. The "functional deficiency of enzyme" includes reduction in the enzymatic activity to such a degree that the bacterium should have L-methionine auxotropy, in addition to substantially complete disappearance of the enzymatic activity. For example, when homoserine dehydrogenase is deficient, the phenotype is expected to be auxotrophy in L-methionine and L-threonine, and the phenotype of deficiency of o-succinylhomoserine sulfhydrylase (e.g., metZ gene product) or methionine synthase (e.g., metE, metH etc.) is also expected to be L-methionine auxotrophy. However, among these, when two or more kinds of enzymes catalyzing the same enzymatic reaction exist in a methanol-utilizing bacterium (as in the case when enzymes catalyzing the same enzymatic reaction separately exist, for example, like metE and metH), it is preferred that the functions of the both enzymes are simultaneously eliminated.

Hereinafter, the method of eliminating an activity of L-methionine synthesis enzyme will be explained by referring to the metA gene as an example. The metA gene can be obtained from a genomic DNA of a microorganism containing the gene, for example, *Methylophilus methylotrophus*, by amplifying the gene using the polymerase chain reaction method (hereafter referred to as "PCR") The genomic DNA can be prepared by well-known methods. Examples of primers useful for PCR include oligonucleotides having the DNA sequences shown in SEQ ID NOS: 7 and 10.

Means for suppressing expression of the metA gene include, for example, a method of suppressing expression of the gene at a transcription level by introducing substitution, deletion, insertion, addition or inversion of one or several nucleotides into a promoter sequence of the gene to reduce the promoter activity (refer to M. Rosenberg & D. Court, Ann. Rev. Genetics, 13, 319 (1979); P. Youderian, S. Bouvier & M. Susskind, Cell, 30, 843–853 (1982)). Furthermore, expression of the MetA protein can also be suppressed at the translational level by substitution, deletion, insertion, addition or inversion of one or several nucleotides into a region between the SD sequence (Shine-Dalgarno sequence) and the initiation codon (refer to J. J. Dunn, E. Buzash-Pollert & F. W. Studier, Proc. Natl. Acad. Sci. U.S.A., 75, p. 2743 (1978)).

Furthermore, for reducing or eliminating the specific activity of homoserine o-acetyltransferase enzyme, modifying or disrupting the coding region of the metA gene by substitution, deletion, insertion, addition or inversion of one or several nucleotides into a nucleotide sequence of the coding region is encompassed.

Site-specific mutagenesis (W. Kramer & H. J. Frits, Methods in Enzymology, 154, 350 (1987)) and a method of treating DNA containing an objective gene with a chemical agent such as sodium hyposulfite or hydroxylamine (D. Shortle & D. Nathans, Proc. Natl. Acad. Sci. U.S.A., 75, 270 (1978)) can be specifically employed in order to introduce substitution, deletion, insertion, addition or inversion of a nucleotide into a gene.

Site-specific mutagenesis is a method using a synthetic oligonucleotide, which can introduce arbitrary substitution, deletion, insertion, addition or inversion into specific base pairs. In order to utilize this method, a plasmid harboring a desired gene that is cloned and has a known DNA nucleotide sequence is first denatured to prepare a single strand. Then, a synthetic oligonucleotide complementary to a region where a mutation is desired to be introduced is synthesized. In this synthesis, the sequence of the synthetic oligonucleotide is not prepared as a completely complementary sequence, but is made to include substitution, deletion, insertion, addition or inversion of an arbitrary nucleotide. Thereafter, the single-stranded DNA and the synthetic oligonucleotide including substitution, deletion, insertion, addition or inversion of an arbitrary nucleotide are annealed, and a complete double-stranded plasmid is synthesized using Klenow fragment of DNA polymerase I and T4 ligase and introduced into competent cells of *Escherichia Coli*. Some of the transformants obtained as described above have a plasmid containing the desired gene in which substitution, deletion, insertion, addition or inversion of an arbitrary nucleotide is fixed.

The recombinant PCR method (PCR Technology, Stockton Press (1989)) can be employed as a similar method that enables introduction of mutation and thereby modification or disruption of the gene.

Furthermore, the method using a treatment with a chemical agent is a method of randomly introducing a mutation including substitution, deletion, insertion, addition or inversion of nucleotide into a DNA fragment including an objective gene by directly treating the DNA fragment with sodium hyposulfite, hydroxylamine or the like.

Expression of the metA gene in a cell can be suppressed by replacing a native gene on a chromosome of a methanol-utilizing bacterium with the gene obtained as described above, which is modified or disrupted by introducing a mutation.

Methods for gene substitution include, but are not limited to, a method utilizing homologous recombination (Experiments in Molecular Genetics, Cold Spring Harbor Laboratory Press (1972); S. Matsuyama & S. Mizushima, J. Bacteriol., 162, 1196 (1985)). The ability to cause homologous recombination is a property generally possessed by methanol-utilizing bacteria. When a plasmid or the like containing a sequence having homology to a sequence on a chromosome is introduced into a bacterial cell, recombination occurs at a site of the sequence having homology at a certain frequency, and the whole plasmid is incorporated into the chromosome. Thereafter, if recombination is caused at the sequence having homology on the chromosome, the plasmid is eliminated again from the chromosome. At this time, the gene introduced with a mutation may be fixed on the chromosome, and the native gene may be eliminated along with the plasmid, depending on the site where the recombination occurs. By selecting such a strain, there can be obtained a strain in which a gene modified or disrupted by introducing a mutation including substitution, deletion, insertion, addition or inversion of a nucleotide substitutes for a native gene on the chromosome.

Furthermore, the inventors of the present invention found that, in *Methylophilus methylotrophus*, introduction of a gene homologous to a desired gene on a chromosome in the form of a linear DNA fragment caused homologous recombination between the desired gene on a chromosome and the homologous gene of the introduced linear DNA fragment in a cell, and thereby gene substitution could be attained, and such a technique can also be applied. An example of gene substitution performed using this technique is described in the examples sections.

To determine if the gene substitution has advanced as intended, for example, a drug resistance marker gene for resistance to an antibiotic may be incorporated into the DNA fragment to be introduced. When a drug resistance marker is used in this way, a gene imparting resistance to a drug such as kanamycin, gentamycin, tetracycline, ampicillin or streptomycin to a methanol-utilizing bacterium is used. Such a marker gene as described above can be used for preparation of a gene to be introduced of which coding region is disrupted by inserting it into the gene. The disrupted-type gene inserted with a marker gene may be prepared by a gene recombination technique using a plasmid DNA as shown in the examples section, or it can also be prepared by simultaneously performing amplification of the gene to be introduced and insertion of the marker gene by crossover PCR.

In the examples section, a *Methylophilus methylotrophus* strain in which the function of the metA gene was disrupted was constructed by replacing the metA gene on a chromosome of *Methylophilus methylotrophus* with a metA gene in which a part of the coding region was deleted and a kanamycin resistance gene was inserted instead of the part of the coding region using the aforementioned method utilizing homologous recombination.

The bacterium of the present invention can be obtained by imparting L-methionine auxotrophy to a methanol-utilizing bacterium having an ability to produce L-lysine as described above. The bacterium of the present invention can also be obtained by imparting an ability to produce L-lysine to a methanol-utilizing bacterium having L-methionine auxotrophy. A methanol-utilizing bacterium, for example, a *Methylophilus methylotrophus* strain which has an ability to produce L-lysine can be obtained by subjecting a strain which does not have an ability to produce L-lysine or has a low ability to produce L-lysine to a mutagenesis treatment to impart to it resistance to an L-lysine analogue such as S-(2-aminoethyl)-L-cysteine (hereafter referred to as "AEC"). Examples of the method for the mutagenesis treatment include, but are not limited to, methods of treating the strain with physical stimulation such as ultraviolet rays, X-rays and γ-rays or a chemical mutagenesis agent such as NTG, as mentioned above for the acquisition of L-methionine auxotrophic strain. Specific examples of *Methylophilus* bacterium having an ability to produce L-lysine obtained as described above include, but are not limited to, *Methylophilus methylotrophus* AJ13608. This strain was bred by imparting the AEC resistance to the *Methylophilus methylotrophus* AS1 strain. The *Methylophilus methylotrophus* AJ13608 was deposited at the National Institute of Bioscience and Human-Technology, Agency of Industrial Science and Technology (currently, National Institute of Advanced Industrial Science and Technology, International Patent Organism Depositary, Tsukuba Central 6, 1-1, Higashi 1-Chome, Tsukuba-shi, Ibaraki-ken, 305–8566, Japan) on Jun. 10, 1999 and received an accession number of FERM P-17416. Then, the deposit was converted to an international deposit under the provisions of the Budapest Treaty on Mar. 31, 2000 and received an accession number of FERM BP-7112.

A *Methylophilus* bacterium having an ability to produce L-lysine can also be bred by introducing or enhancing DNA carrying genetic information involved in the biosynthesis of L-lysine with a genetic recombination technique. The gene or genes to be introduced encodes for an enzyme of the biosynthetic pathway of L-lysine such as dihydrodipicolinate synthase and succinyl diaminopimelate transaminase. In the case of a gene of a enzyme suffering from feedback inhibition by L-lysine such as dihydrodipicolinate synthase (DDPS), it is preferable to use a mutant gene coding for the enzyme for which inhibition is desensitized. Examples of such a mutant gene include, but are not limited to, the dapA*24 gene (coding for DDPS of which histidine residue at position 118 is replaced with a tyrosin residue) of *E. coli* described in WO95/16042 and so forth. The other genes mentioned above are also described in this international patent publication. In the description of the international patent publication, a gene coding for tetrahydrodipicolinate succinylase and a gene coding for succinyl diaminopimelate transaminase are described with exchanged each other.

Furthermore, an ability to produce an L-amino acid can also be improved by enhancing an activity of a protein involved in secretion of the L-amino acid to the outside of the cells. For example, as a protein involved in secretion of L-lysine to the outside of the cells, the LysE protein encoded by the lysE gene is known (M. Vrljic, H. Sahm and L. Eggeling, Molecular Microbiology 22, pp. 815–826 (1996); International Patent Publication WO97/23597). The inventors of the present invention confirmed that a wild-type lysE gene derived from a *Brevibacterium* bacterium does not function in a *Methylophilus* bacterium or *Methylobacillus* bacterium, but it could be modified to function in a methylotroph. Examples of such a modified LysE protein include LysE24 described in the examples herein.

The LysE protein that is encoded by the lysE gene has six hydrophobic helix regions. Some of these hydrophobic regions are estimated to be transmembrane domains. It is also estimated that a region between the third and fourth regions relative to the N-terminus is hydrophilic and has a loop structure. In the present invention, this hydrophilic region is called a loop region. The nucleotide sequence of wild-type lysE and the amino acid sequence of the LysE protein of *Brevibacterium lactofermentum* 2256 are shown in SEQ ID NOS: 17 and 18, respectively. In this amino acid sequence, hydrophobic helix regions correspond to the amino acid numbers 5–20, 37–58, 67–93, 146–168, 181–203 and 211–232. The loop region corresponds to the amino acid numbers 94–145.

The inventors of the present invention found that the lysE gene was lethal in a methanol-utilizing bacterium, but that a DNA encoding a variant of the LysE protein that did not have the loop region or substantially consisted only of the hydrophobic helixes promoted the secretion of L-lysine and/or L-arginine to the outside of a methanol-utilizing bacterium. The DNA of the present invention encodes such a mutant LysE protein lacking the aforementioned loop region that is contained in a wild-type LysE protein or that substantially consists of the only hydrophobic helixes.

The aforementioned mutant LysE is not particularly limited so long as it has one or more hydrophobic helixes and when expressed results in increased secretion of L-lysine, L-arginine or both when it is introduced into a methanol-utilizing bacterium. Specifically, a DNA coding for a mutant LysE that has all of the first to sixth hydrophobic helixes relative to the N-terminus is encompassed. More specifically, a DNA encoding a peptide containing the first to third hydrophobic helixes relative to the N-terminus, and encoding a peptide containing the fourth to sixth hydrophobic helixes relative to the N-terminus is encompassed. The aforementioned lysE24 is an example of the mutant type lysE that codes for a peptide containing the first to third hydrophobic helixes and a peptide containing the fourth to sixth hydrophobic helixes. The lysE24 gene is introduced by a mutation with a stop codon downstream from the region coding for the third hydrophobic helix. The inventors of the present invention confirmed that, if a region downstream from this stop codon was deleted, the mutant lysE24 gene did not cause L-lysine to accumulate in the medium when expressed in *Methylophilus methylotrophus* AS1 strain. Therefore, it is estimated that a peptide containing the first to third hydrophobic helixes and a peptide containing the fourth to sixth hydrophobic helixes are separately translated and function in a methanol-utilizing bacterium. The results show that introduction of the lysE24 gene into a methanol-utilizing bacterium will result in improvement of the production of L-lysine or L-arginine.

Any microorganism can be used to generate a DNA encoding a protein involved in secretion of L-lysine to the outside of a cell, i.e., the lysE gene or its homologous gene, so long as it has a variant of the gene that can express the L-lysine secretion activity in a methanol-utilizing bacterium. Specifically, examples of such microorganisms include but are not limited to coryneform bacteria such as *Corynebacterium glutamicum* and *Brevibacterium lactofermentum*, *Escherichia* bacteria such as *Escherichia coli*, *Pseudomonas* bacteria such as *Pseudomonas aeruginosa*, *Mycobacterium* bacteria such as *Mycobacterium tuberculosis* and so forth.

Examples of the homologous gene of lysE include a DNA encoding a protein which is hybridizable under stringent conditions with a probe having the nucleotide sequence of SEQ ID NO: 17 or a part thereof, and encodes a protein exhibiting the function of the LysE protein in a methanol-utilizing bacterium as the result of the aforementioned amino acid substitution. The aforementioned "stringent conditions" include conditions under which a so-called specific hybrid is formed, and a non-specific hybrid is not formed. It is difficult to clearly express this condition using any numerical value. However, for example, the stringent conditions include a condition under which DNAs having high homology, for example, DNAs having homology of 80% or more, preferably 90% or more, more preferably 95% or more, are hybridized with each other, whereas DNAs having homology lower than the above do not hybridize with each other. Alternatively, the stringent conditions include conditions whereby DNAs hybridize with each other at a salt concentration corresponding to typical washing conditions of Southern hybridization, i.e., 1×SSC, 0.1% SDS, preferably 0.1×SSC, 0.1% SDS, at 60° C.

A partial sequence of the nucleotide sequence of SEQ ID NO: 17 can also be used as the probe. Such a probe can be prepared by PCR using oligonucleotides prepared based on the nucleotide sequence of SEQ ID NO: 17 as primers and a DNA fragment containing the nucleotide sequence of SEQ ID NO: 17 as a template. When a DNA fragment having a length of about 300 bp is used as the probe, the washing conditions of hybridization can be, for example, 2×SSC, 0.1% SDS at 50° C.

In order to enhance expression of the amino acid secretion gene or a gene of the L-lysine biosynthesis system in a methanol-utilizing bacterium, the gene fragment is ligated to a vector which is able to function in methanol-utilizing bacterium, preferably a multi-copy type vector, to prepare a recombinant DNA which is then used to transform the host methanol-utilizing bacterium. Alternatively, the gene can be incorporated into a transposon and introduced into chromosome. Furthermore, a promoter that induces potent transcription in a methanol-utilizing bacterium can be ligated upstream from the gene.

To introduce a gene into *Methylophilus* bacteria and enhance its expression, the gene may be ligated to a vector autonomously replicable in a cell of *Methylophilus* bacteria to construct a recombinant DNA, which is then used to transform a *Methylophilus* bacterium by electroporation or the like. In addition, it is also possible to incorporate a target gene into a host chromosome by a method using transduction, transposon (D. E. Berg, and C. M. Berg, Bio/Technol., 1, p. 417, 1983), Mu phage, (Japanese Patent Laid-open (Kokai) No. 2-109985) or homologous recombination (Experiments in Molecular Genetics, Cold Spring Harbor Lab. (1972)).

The vectors that functions in *Methylophilus* bacteria include, but are not limited to, a plasmid that can autonomously replicate in *Methylophilus* bacteria. Specifically, examples include RSF1010, which is a wide host range vector, and derivatives thereof, for example, pAYC32 (A. Y. Chistorerdov, Y. D. Tsygankov, Plasmid, 16, pp. 161–167 (1986)), pMFY42 (Gene, 44, p. 53 (1990)), pRP301, pTB70 (Nature, 287, p. 396, (1980)) and so forth.

The vector that functions in *Methylobacillus* bacteria is, but is not limited to, a plasmid that can autonomously replicate in *Methylobacillus* bacteria. Specifically, examples include RSF1010, which is a wide host range vector, and derivatives thereof, for example, pMFY42 (Gene, 44, p. 53 (1990)) and so forth.

Any method can be used to introduce a recombinant DNA molecule into a *Methylophilus* bacterium, so long as it provides sufficient transformation efficiency. For example, electroporation can be used (Canadian Journal of Microbiology, 43, p. 197 (1997)).

Production of L-Lysine Using Methanol-Utilizing Bacterium Imparted with L-Methionine Auxotrophy Culturing a methanol-utilizing bacterium imparted with L-methionine auxotrophy by disruption of metA gene or mutagenesis treatment and having an ability to produce L-lysine obtained as described above in a medium added with an appropriate amount of L-methionine results in production of a marked amount of L-lysine and accumulation of the produced L-lysine in the medium. Thus, utilization of the methanol-utilizing bacterium of the present invention imparted with L-methionine auxotrophy and having an ability to produce L-lysine is effective for improvement of accumulation amount of L-lysine.

The medium used for producing L-lysine is a typical medium that contains a carbon source, nitrogen source, inorganic ions and other organic trace nutrients as required. The main carbon source is methanol. However, sugars such as glucose, lactose, galactose, fructose, and starch hydrolysate; alcohols such as glycerol and sorbitol, and organic acids such as fumaric acid, citric acid, succinic acid and pyruvic acid may be used together. The expression "methanol is used as the main carbon source" means that methanol content in the total carbon source is 50% (w/w) or more, preferably 80% (w/w) or more. If methanol is used as the main carbon source, the concentration thereof is usually between 0.001% to 4% (w/v), preferably between 0.1% to 2% (w/v). Furthermore, when glucose etc. is added, the concentration thereof is usually between 0.1% to 3% (w/w), preferably between 0.1% to 1% (w/v).

Furthermore, the medium must contain an appropriate amount of L-methionine. Although the content is preferably adjusted depending on the culture conditions, it is usually within such a range that the L-methionine content is not sufficient, and therefore the growth of the bacterium should be limited, and allows the most efficient production of L-lysine by the bacterium. For example, the L-methionine content in the medium is preferably between 0.01 to 1 g/L.

As the nitrogen source, inorganic ammonium salts such as ammonium sulfate, ammonium chloride and ammonium phosphate, organic nitrogen such as soybean hydrolysate, ammonia gas, aqueous ammonia and so forth can be used.

As the inorganic ions (or sources thereof), a small amount of potassium phosphate, magnesium sulfate, iron ions, manganese ions and so forth are added to the medium. As the organic trace nutrients, vitamin $B_1$, yeast extract and so forth may be added to the medium in a suitable amount.

The culture is preferably performed for within about 16 to 72 hours under aerobic conditions. The culture temperature is controlled to be between 25° C. to 45° C., and pH is controlled to be between 5 to 8 during the culture. Inorganic or organic acidic or alkaline substances, ammonia gas and so forth can be used to adjust the pH.

After completion of the culture, L-lysine can be collected from fermentation broth by, for example, typical methods utilizing ion exchange resins, precipitation and other known methods in combination.

EXAMPLES

Hereinafter, the present invention will be explained more specifically with reference to the following non-limiting examples.

Example 1

Preparation of L-Methionine Auxotrophic Strain from Wild-Type Strain of *Methylophilus* Bacterium A wild-type strain of *Methylophilus methylotrophus*, AS1 strain (NCIMB 10515), was treated with N-methyl-N'-nitro-N-nitrosoguanidine (NTG) to isolate an L-methionine auxotrophic strain as described below. First, one day before the treatment with NTG, the wild-type strain AS1 was inoculated into 50 mL of the SEII medium (composition: 1.9 g/L of $K_2HPO_4$, 5.0 g/L of $(NH_4)_2SO_4$, 1.56 g/L of $NaH_2PO_4 \cdot 2H_2O$, 0.2 g/L of $MgSO_4 \cdot 7H_2O$, 0.72 mg/L of $CaCl_2 \cdot 6H_2O$, 5 µg/L of $CuSO_4 \cdot 5H_2O$, 25 µg/L of $MnSO_4 \cdot 5H_2O$, 23 µg/L of $ZnSO_4 \cdot 7H_2O$, 9.7 mg/L of $FeCl_3 \cdot 6H_2O$, 1% (v/v) of methanol) and cultured overnight at 37° C. with shaking. An NTG solution was prepared at a concentration of 10 mg/ml (prepared by dissolving NTG in dimethyl sulfoxide (DMSO)).

On the next day, the cultured cells were collected by centrifugation at 4° C., and 50 mL of ice-cooled 50 mM potassium phosphate buffer (pH 7.0) was added to the cells to suspend them. Then, the suspension was recentrifuged, and the supernatant was removed to wash the cells once. The cells were suspended in 2 ml of the same buffer and divided into two of Eppendorf tubes in equal volumes. One of them was used for the NTG treatment, and the other one was used as a control, not treated with NTG Ten µl of the NTG solution or a DMSO solution not containing NTG was added to each tube. At this stage, the final concentration of NTG in the sample subjected to the NTG treatment was 0.1 mg/mL. These samples were treated at 37° C. for 5 minutes and left on ice for 2 minutes, and then each sample was centrifuged at 15000 rpm for 2 minutes to collect the cells.

The cells collected from each sample were washed twice with ice-cooled SEII medium, then suspended in 3 ml of the SEII+MT medium (composition: SEII medium containing L-methionine (1 g/L) and L-threonine (10 g/L)) and cultured overnight at 37° C. At this stage, a part of each sample was extracted and inoculated on the SEII agar medium (composition: SEII medium containing 1.5% (w/v) of agar), and the number of the appeared colonies (number of viable bacteria) was used to calculate the rate of death due to the NTG treatment. The rate of death was represented as [the number of viable cells in the sample subjected to the NTG treatment/the number of viable cells in the sample treated only with the DMSO solution].

On the next day of the NTG treatment, a part of the aforementioned culture broth was inoculated into to the SEII+MT medium and incubated at 37° C. to allow proliferation of the bacterium. When the value of the absorbance of the culture broth at a wavelength of 660 nm (OD 660 nm) became about 0.5, an equal volume of 20% DMSO solution (final concentration: 10%) was added for preservation of the cells, and the culture broth was sufficiently stirred and then stored at −80° C.

Furthermore, a part of the culture broth was inoculated on the SEII-MT agar medium and the SE-II agar medium containing 50 μg/ml of antibiotic, streptomycin (Sm), and the emerging frequency of Sm-resistant strains, i.e., the mutation rate, was measured. As a result, the mutation rate was about $4 \times 10^{-6}$.

The stock solution of the bacterium treated with NTG was thawed at room temperature, and 1 to $1/10^7$-fold serial dilutions thereof were prepared and inoculated on the SEII-MT agar medium. The cells were cultured at 37° C. for two days, and the dilution degree providing formation of 100 to 200 colonies per one agar plate was confirmed. Then, the stock solution of the bacterium was newly diluted to that concentration and inoculated on the SEII+MT agar medium. The cells were cultured at 37° C. for three days, and then the colonies that appeared were replicated on an SEII agar medium plate and SEII+MT agar medium plate to select the colonies that could grow on the SEII+MT agar medium, but could not grow on the SEII agar medium. Then, the selected colonies were successively inoculated on each of the SEII agar medium, SEII+M agar medium (composition: agar medium containing L-methionine (1 g/L) in the SEII medium), SEII+T agar medium (composition: agar medium containing L-threonine (10 g/L) in the SEII medium) and SEII+MT agar medium, and it was confirmed whether the amino acid auxotrophy of those clones was auxotrophy in L-methionine, L-threonine or both.

As a result, two of the L-methionine auxotrophic strains and one of the L-threonine auxotrophic strains could be obtained. These were designated as the MR102 strain, MR103 strain and TR115 strain, respectively. Any strain that required both of the amino acids for its growth could not be obtained in this experiment.

Example 2

<1> Introduction of LysE Gene Derived from *Brevibacterium* Bacterium into *Methylophilus* Bacterium (1) Construction of pRSlysE24

In order to introduce lysE gene which encodes a protein showing activity to excrete lysine in *Corynebacterium glutamicum* into a *Methylophilus* bacterium, a known plasmid pRS (refer to International Patent Publication in Japanese (Kohyo) No. 3-501682) was used to construct a plasmid pRSlysE for expression of lysE. pRS is a plasmid having the vector segment of the pVIC40 plasmid (International Patent Publication WO90/04636, International Patent Publication in Japanese No. 3-501682) and obtained from pVIC40 by deleting a DNA region encoding the threonine operon contained in the plasmid. The plasmid pVIC40 is derived from a wide host range vector plasmid pAYC32 (Chistorerdov, A. Y., Tsygankov, Y. D., Plasmid, 1986, 16, 161–167), which is a derivative of RSF1010.

First, a plasmid pRStac having the tac promoter was constructed from pRS. The pRStac plasmid was constructed as follows. The pRS vector was digested with restriction enzymes EcoRI and PstI and added to a phenol/chloroform solution and mixed to terminate the reaction. After the reaction mixture was centrifuged, the upper layer was collected, and DNAs were collected by ethanol precipitation and separated on 0.8% agarose gel. A DNA fragment of 8 kilobase pairs ("kbp") was collected using EASY TRAP Ver. 2 (DNA collection kit, Takara Shuzo). On the other hand, the tac promoter region was amplified by PCR using the pKK223-3 plasmid (expression vector, Pharmacia) as a template and the primers shown in SEQ ID NOS: 1 and 2 (a cycle consisting of denaturation at 94° C. for 20 seconds, annealing at 55° C. for 30 seconds and extension reaction at 72° C. for 60 seconds was repeated for 30 cycles). Pyrobest DNA polymerase (Takara Shuzo) was used for PCR. The DNA fragment containing the amplified tac promoter was purified using PCR prep (Promega) and then digested at the restriction enzyme sites preliminarily designed in the primers, i.e., at EcoRI and EcoT22I sites. Then, the reaction mixture was added to a phenol/chloroform solution and mixed to terminate the reaction. After the reaction mixture was centrifuged, the upper layer was collected and DNAs were collected by ethanol precipitation and separated on 0.8% agarose gel. A DNA fragment of about 0.15 kbp was collected using EASY TRAP Ver. 2.

The digestion product of the pRS vector and the tac promoter region fragment prepared as described above were ligated using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes to obtain pRStac. A plasmid in which the transcription directions of the streptomycin resistance gene on the pRS vector and the tac promoter were identical to each other was selected as pRStac.

pRStac obtained as described above was digested with Sse8387I (Takara Shuzo) and SapI (New England Biolabs), added to a phenol/chloroform solution and mixed to terminate the reaction. After the reaction mixture was centrifuged, the upper layer was collected and DNAs were collected by ethanol precipitation and separated on 0.8% agarose gel to obtain a DNA fragment of about 9.0 kbp.

The lysE gene fragment was also amplified by PCR using chromosome extracted from the *Brevibacterium lactofermentum* 2256 strain (*Corynebacteirum glutamicum* ATCC13869) as a template and the primers shown in SEQ ID NOS: 5 and 6 (denaturation at 94° C. for 20 seconds, annealing at 55° C. for 30 seconds and extension reaction at 72° C. for 90 seconds). Pyrobest DNA polymerase (Takara Shuzo) was used for PCR. To enable expression of the lysE gene in a *Methylophilus* bacterium, the primers were designed so that nucleotides of 9–15 bp from the translation initiation codon of the lysE gene should be replaced with a sequence that is known to function in a *Methylophilus* bacterium (Wyborn, N. R., Mills, J., Williamis, S. G. and Jones, C. W., Eur. J. Biochem., 240, 314–322 (1996)). The resulting fragment was purified using PCR prep (Promega) and then digested with Sse8387I and SapI. The reaction mixture was added to a phenol/chloroform solution and mixed to terminate the reaction. After the reaction mixture was centrifuged, the upper layer was collected and DNAs were collected by ethanol precipitation and further collected from 0.8% agarose gel.

The digestion product of the pRStac vector and the lysE gene region fragment prepared as described above were ligated using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and the structure of each plasmid was confirmed by digestion with restriction enzymes and determination of nucleotide sequence to obtain pRSlysE. In pRSlysE, the lysE gene was positioned so that its transcription direction is the same as that of the tac promoter.

(2) Introduction of pRSlysE into *Methylophilus* Bacterium pRSlysE obtained as described above was introduced into *Methylophilus methylotrophus* AS1 strain (NCIMB 10515) by electroporation (Canadian Journal of Microbiology, 43, 197 (1997)). In addition, pRS was also introduced into the AS1 strain as a control in the same manner as that for pRSlysE. As a result, several thousands of colonies were obtained per 1 µg of DNA with pRS used as a control, whereas only several colonies were obtained with pRSlysE.

When plasmids were extracted from transformant strains estimated to contain pRSlysE and their nucleotide sequences were investigated, it was found that a spontaneous mutation was introduced in a region encoding lysE for all the investigated plasmids, and in some cases, a nonsense mutation was introduced having a codon encoding an amino acid replaced by a stop codon that terminated the translation. Furthermore, in other plasmids, deletion of lysE gene was observed. It was considered that, in either case, the function of lysE carried by such plasmids was lost.

As described above, the introduction frequency of pRSlysE carrying the full length lysE gene into *Methylophilus methylotrophus* was extremely low, and only plasmids having a lysE mutant gene containing a mutation that eliminated the function could be introduced. Considering these facts in combination, it was estimated that the introduction of the lysE gene into *Methylophilus methylotrophus* would have a lethal effect. This suggests that the lysE gene cannot universally function for the secretion of L-lysine in heterogenous bacteria.

The *Methylophilus methylotrophus* AS1 strain harboring pRSlysE introduced with a mutation was applied to an SEII plate containing 20 mg/L of streptomycin and cultured overnight at 37° C. Then, the cells of about 0.3 cm² of the medium surface were scraped, inoculated into SEII production medium (20 ml) containing 20 mg/L of streptomycin, and cultured at 37° C. for 34 hours with shaking. After completion of the culture, the cells were removed by centrifugation and the L-lysine concentration in the culture supernatant was determined using an amino acid analyzer (Nihon Bunko, high speed liquid chromatography). As a result, substantially no strain was obtained in which secretion of L-lysine was enhanced in spite of introduction of the mutant lysE gene.

<2> Acquisition of the Gene Providing Activity for Secreting L-Lysine in *Methylophilus* Bacterium As described in the preceding section, it was suggested that the known lysE gene is lethal in *Methylophilus* bacteria, and as a result, many mutant genes for which function was lost were subsequently obtained.

During analysis of pRSlysE containing a mutation, a mutant lysE gene that functioned in *Methylophilus* bacteria but was not lethal was obtained.

This mutant lysE gene was designated as lysE24 gene. When the nucleotide sequence of the lysE24 gene was analyzed, it was found that this mutation did not result in an amino acid substitution, but a nonsense mutation introducing a stop codon around the center of the translation region of lysE. In lysE24, T (thymine) was inserted after G (guanine) at position 355 of the wild-type lysE gene shown in SEQ ID NO: 17. This plasmid having lysE24 was designated as pRSlysE24.

The *E. coli* JM109 strain transformed with pRSlysE24 was designated as AJ13830, and this strain was deposited at the independent administrative corporation, National Institute of Advanced Industrial Science and Technology, International Patent Organism Depositary on Jun. 4, 2001 and received an accession number of FERM P-18369. Then the deposit was converted to an international deposit under the provisions of the Budapest Treaty on May 13, 2002 and received an accession number of FERM BP-8040.

Example 3

Construction of Lysine-Producing Plasmids pSEA10 and pSEA12

<1> Construction of Plasmid pRSdapA Having dapA* Gene

There was prepared a plasmid having a gene (dapA*) encoding dihydrodipicolinate synthase that was not subject to feedback inhibition by L-lysine as an L-lysine biosynthesis system enzyme gene.

pRStac prepared in Example 2 was digested with Sse8387I and XbaI, added to a phenol/chloroform solution and mixed to terminate the reaction. After the reaction mixture was centrifuged, the upper layer was collected, and DNAs were collected by ethanol precipitation and separated on 0.8% agarose gel to collect a DNA fragment of about 9 kbp.

The known plasmid RSFD80 (refer to WO90/16042) containing the dapA* gene fragment was used as a template to amplify dapA* via PCR using the primers shown in SEQ ID NOS: 3 and 4 (denaturation at 94° C. for 20 seconds, annealing at 55° C. for 30 seconds and extension reaction at 72° C. for 60 seconds). Pyrobest DNA polymerase (Takara Shuzo) was used for PCR. The obtained dapA* fragment was purified using PCR prep (Promega) and then digested with restriction enzymes Sse8387I and XbaI. The reaction mixture was added to a phenol/chloroform solution and mixed to terminate the reaction. After the reaction mixture was centrifuged, the upper layer was collected and DNAs were collected by ethanol precipitation and separated on 0.8% agarose gel to collect a DNA fragment of about 0.1 kbp.

The digestion product of the pRStac vector and the dapA* gene region fragment prepared as described above were ligated using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies that appeared on the agar medium were each inoculated into LB liquid medium containing 20 mg/L of streptomycin and cultured at 37° C. for 8 hours with shaking. Plasmid DNA was extracted from each culture broth by the alkali-SDS method and structure of each plasmid was confirmed by digestion with restriction enzymes and determination of nucleotide sequence to obtain a pRSdapA plasmid. In the pRSdapA plasmid, the dapA* gene was positioned so that its transcription direction is the same as the tac promoter.

The *E. coli* JM109 strain transformed with the pRSdapA plasmid was designated as AJ13831, and this strain was deposited at the independent administrative corporation, National Institute of Advanced Industrial Science and Technology, International Patent Organism Depositary on Jun. 4, 2001 and received an accession number of FERM P-18370. Then, the deposit was converted to an international deposit under the provisions of the Budapest Treaty on May 13, 2002, and received an accession number of FERM BP-8041.

<2> Construction Plasmids pSEA10 and pSEA12 Having LysE24 and dapA*

A plasmid consisting of the pRSlysE24 plasmid inserted with the dapA* gene was constructed to evaluate effect of combining lysE24 and dapA*.

pRSlysE24 prepared in Example 2 was digested with the restriction enzyme SapI, and blunt-ended using DNA Blunting Kit (Takara Shuzo). The plasmid pRSdapA having dapA* was digested with restriction enzymes EcoRI and SapI, and a fragment of about 1 kbp containing the tac promoter and the dapA* region was separated on 0.8% agarose gel. This fragment was collected using EASY TRAP Ver. 2 (Takara Shuzo). This fragment was blunt-ended as described above and ligated to the aforementioned digestion product of pRSlysE24 using DNA Ligation Kit Ver. 2 (Takara Shuzo).

The aforementioned ligation reaction solution was used to transform *Escherichia coli* (*E. coli* JM109 competent cells, Takara Shuzo). The cells were plated on LB agar medium containing 20 mg/L of streptomycin. After the agar plate was incubated overnight at 37° C., many colonies appeared on the agar medium. Among them, 8 colonies were each inoculated into LB liquid medium containing 20 mg/L of streptomycin and cultured at 37° C. for 8 hours with shaking. Plasmid DNA was extracted from each culture broth by the alkali-SDS method, and structure of each plasmid was confirmed by digestion with restriction enzymes and determination of nucleotide sequence to obtain pSEA10 and pSEA12 plasmids. As for these plasmids, the lysE24 gene and the dapA* gene were positioned so that their transcription directions are reverse to each other in the former, and they were positioned so that their transcription directions are identical to each other in the latter.

Example 4

Introduction of pSEA12 into *Methylophilus Methylotrophus* AS1 Strain and L-Methionine Auxotrophic Strains (MR102 Strain and MR103 Strain) (Effect of Impartation of L-Methionine Auxotrophy on Lysine Production)

The plasmid carrying the genes was introduced into the *Methylophilus methylotrophus* wild strain, AS1 strain, and two of the L-methionine auxotrophic strains, MR102 strain and MR103 strain, by the conjugal transfer method. On the previous day of the conjugation procedure, the AS1 strain, MR102 strain and MR103 strain as recipient strains were each cultured in 15 mL of the SEII+M medium (composition: SEII medium containing 0.5 g/L of L-methionine). The *E. coli* HB101 strain harboring pRK2013 was inoculated to 10 mL of the LB (Km) medium (LB medium containing 25 μg/ml of kanamycin) as a mobilizer, *E. coli* JM109 strain harboring pSEA12 was inoculated to 3 mL of LB (Sm) medium (LB medium containing 20 μg/ml of streptomycin) as a donor, and they were cultured.

On the next day, each culture broth was centrifuged to collect the cells, and the cells were washed once with the LB medium for the *E. coli* HB 101 strain harboring pRK2013 and the *E. coli* JM109 strain harboring pSEA12. Furthermore, for three strains of the aforementioned methanol-utilizing bacteria, the cells were also collected and then washed with the SEII medium. Then, the *E. coli* cells of each kind were suspended in the LB medium, and the cells of the methanol-utilizing bacteria were suspended in the SEII medium. Then, appropriate volumes of the suspensions were mixed on the LB agar medium using a loop and incubated at 37° C. for 4 hours to allow conjugative transfer of pSEA12 into each of the AS1 strain, MR102 strain and MR103 strain. Then, the cells of each strain were scraped from the agar medium and spread on the SEII+M (Sm) agar medium (medium composition: SEII+M agar medium containing Sm (50 μg/(ml)) and cultured at 37° C. for two days for selection of transformants. Each single colony that appeared on the medium was further spread twice on a fresh SEII+M (Sm) agar medium to isolate the MR102(pSEA12) strain and MR103(pSEA12) strain as objective strains, and AS1(pSEA12) strain as a control strain.

Each of the three above-mentioned strains was applied to the SEII+M (Sm) agar plate and cultured overnight at 37° C. Then, the cells grown on the medium surface were scraped for about 3 cm$^2$ (square centimeters), inoculated into the SEII production medium (20 ml) containing L-methionine at various concentrations and cultured at 37° C. for 48 hours with shaking. After completion of the culture, the cells were removed by centrifugation, and the L-lysine concentration in the culture supernatant was determined using an amino acid analyzer (Nihon Bunko, high speed liquid chromatography). As a result, L-lysine accumulation in the medium obtained with the AS1(pSEA12) strain was 0.96 g/L at most. However, the pSEA12-introduced strains of the MR102 strain and MR103 strain showed L-lysine accumulations in the medium of 1.675 g/L and 1.57 g/L, respectively, when 0.075 g/L of L-methionine was added to the production medium, and thus the L-lysine accumulation in the medium was markedly improved.

Example 5

Preparation of L-Methionine Auxotrophic Strain (MR701 Strain) from *Methylophilus methylotrophus* AS1 Strain and Preparation of Lysine-Producing Bacterium by Introduction of pSEA10 into the Same Strain <1> Preparation of MetA Gene-disrupted Strain From the *Methylophilus methylotrophus* AS1 strain, a fragment for gene disruption was prepared for obtaining an L-methionine auxotrophic strain by gene disruption. As the gene to be disrupted, a gene region was selected that has high homology to the metA gene of the *Mycobacterium tuberculosis* H37Rv strain (GenBank Accession No. CAA 17113), which is thought to encode homoserine o-acetyltransferase. This region can be amplified by PCR using the DNA primers shown in SEQ ID NOS: 7 and 10 (reaction conditions: TaKaRa Ex Taq was used, a cycle of reaction steps of denaturation: 94° C. for 30 seconds, annealing: 60°

C. for 30 seconds and DNA strand extension reaction: 72° C. for 4 minutes was repeated for 25 cycles). The DNA sequence of the region and the amino acid sequence encoded thereby are shown in SEQ ID NOS: 15 and 16, and the gene was designated as the metA gene.

In order to obtain a chromosomal DNA from wild-type strain AS1, the AS1 strain was inoculated in 50 mL of SEII medium (composition: 5 g/L of $(NH_4)_2SO_4$, 1.9 g/L of $K_2HPO_4$, 1.56 g/L of $NaH_2PO_4 \cdot 2H_2O$, 200 mg/L of $MgSO_4 \cdot 7H_2O$, 72 mg/L of $CaCl_2 \cdot 6H_2O$, 5 μg/L of $CuSO_4 \cdot 5H_2O$, 25 μg/L of $MnSO_4 \cdot 5H_2O$, 23 μg/L of $ZnSO_4 \cdot 7H_2O$, 9.7 mg/L of $FeCl_3 \cdot 6H_2O$, 0.5% (v/v) of methanol) and cultured overnight at 37° C. with shaking. Then, the culture broth was centrifuged to collect the cells, and a chromosomal DNA was prepared using a commercially available kit (Genomic DNA Purification Kit (produced by Edge Biosystems).

The obtained chromosomal DNA was used as a template with the DNA primers shown in SEQ ID NOS: 7 and 8 to perform PCR (reaction conditions: TaKaRa Ex Taq was used, a cycle consisting reaction steps of denaturation: 94° C. for 30 seconds, annealing: 60° C. for 30 seconds, and DNA strand extension reaction: 72° C. for 2 minutes was repeated for 25 cycles) and thereby obtain a fragment of about 1.3 kb. PCR was also performed using the primers shown in SEQ ID NOS: 9 and 10 under the same conditions to obtain a DNA fragment having a size of about 2.0 kb.

PCR was also performed using the plasmid pKD4 (GenBank Accession No. AY048743, Datsenko, K. A. et al., Proc. Natl. Acad. Sci. U.S.A., 97 (12), 6640–6645, 2000) as a template and the primers shown in SEQ ID NOS: 11 and 12 under the same conditions as mentioned above to obtain a DNA fragment containing a kanamycin resistance gene (about 1.5 kb).

The three kinds of DNA fragments mentioned above were mixed and used as a template together with the primers shown in SEQ ID NOS: 13 and 14 to perform PCR (reaction conditions: TaKaRa Ex Taq was used, a cycle consisting reaction steps of denaturation: 94° C. for 30 seconds, annealing: 60° C. for 30 seconds and DNA strand extension reaction: 72° C. for 4 minutes and 30 seconds was repeated for 25 cycles) and thereby obtain a fragment of about 4.2 kb. The fragment was purified using a commercially available kit (Wizard PCR Preps DNA Purification System produced by Promega) and then subjected to ethanol precipitation, and the precipitates were suspended in TE. This DNA solution was used in the following operation as a fragment for gene disruption. This gene fragment had a structure consisting of the metA gene inserted with the kanamycin resistance gene.

Then, the gene fragment described above was introduced into the *Methylophilus methylotrophus* AS1 strain. The electroporation method (Canadian Journal of Microbiology, 43, 197 (1997)) was used for the transformation. The cells after the electroporation were applied to the SEII agar medium (20 mg/L of kanamycin and 0.5 g/L of L-methionine were added). After 48 hours of culture, several tens of colonies appeared. Among them, 13 strains were randomly selected and examined for L-methionine auxotrophy. As a result, all of the strains exhibited L-methionine auxotrophy. The L-methionine auxotrophic strain obtained by the gene disruption was designated as the MR701 strain.

Disruption of the objective gene was confirmed by the PCR method. That is, the aforementioned colonies that appeared were suspended in 20 μl of sterilized water, added with 5 μl of 1 mg/ml Proteinase K and 25 μl of a buffer (40 mM Tris, 0.5% Tween 20, 1% Nonidet P-40, 1 mM EDTA (adjusted to pH 8.0 with HCl)) and then reacted at 60° C. for 20 minutes and at 95° C. for 5 minutes. This reaction mixture was used as a template for PCR. PCR was performed using the sequences shown in SEQ ID NOS: 7 and 10 as primers (reaction conditions: TaKaRa Ex Taq was used, a cycle consisting reaction steps of denaturation: 94° C. for 30 seconds, annealing: 60° C. for 30 seconds and DNA strand extension reaction: 72° C. for 4 minutes and 30 seconds was repeated for 25 cycles) to confirm the disruption of the objective gene.

<2> Evaluation of L-Lysine Productivity of metA Gene-Disrupted Strain

Then, pSEA10 described in Example 3 was introduced into the MR701 strain obtained as described above, and L-lysine production of the strain was investigated. pSEA10 was introduced into the MR701 strain by electroporation, and the obtained transformant was designated as MR701 (pSEA10). The AS1(pSEA10) strain was spread on the SEII (Sm) agar medium (SEII medium containing 50 μg/ml of streptomycin), and the MR701(pSEA10) strain was spread on the SEII+M (Sm Km) agar medium (SEII medium containing 0.5 g/L of L-methionine and 50 μg/ml of streptomycin and 20 μg/ml of kanamycin). After the cells were cultured overnight at 37° C., the cells grown on the medium surface were scraped for about 3 cm² (square centimeters), inoculated into the SEII production medium (20 ml) containing 0.075 g/L of L-methionine (50 μg/ml of streptomycin was added) and cultured at 37° C. for 48 hours with shaking. After completion of the culture, the cells were removed by centrifugation, and the L-lysine concentration in the culture supernatant was determined using an amino acid analyzer (Nihon Bunko, high speed liquid chromatography). As a result, it was found that L-lysine accumulation in the medium of the AS1(pSEA10) strain was 0.97 g/L, whereas the MR701(pSEA10) strain showed L-lysine accumulation in the medium of 1.52 g/L, and thus it could be confirmed that the L-lysine production was improved by impartation of L-methionine auxotrophy.

EXPLANATION OF SEQUENCE LISTING

SEQ ID NO: 1: Primer for amplification of tac promoter region
SEQ ID NO: 2: Primer for amplification of tac promoter region
SEQ ID NO: 3: Primer for amplification of dapA* gene
SEQ ID NO: 4: Primer for amplification of dapA* gene
SEQ ID NO: 5: Primer for amplification of lysE gene
SEQ ID NO: 6: Primer for amplification of lysE gene
SEQ ID NO: 7: Primer for amplification of metA gene
SEQ ID NO: 8: Primer for amplification of metA gene
SEQ ID NO: 9: Primer for amplification of metA gene
SEQ ID NO: 10: Primer for amplification of metA gene
SEQ ID NO: 11: Primer for amplification of kanamycin resistance gene
SEQ ID NO: 12: Primer for amplification of kanamycin resistance gene
SEQ ID NO: 13: Primer for amplification of fragment for disruption of metA gene
SEQ ID NO: 14: Primer for amplification of fragment for disruption of metA gene
SEQ ID NO: 15: Nucleotide sequence of metA
SEQ ID NO: 16: Amino acid sequence encoded by metA
SEQ ID NO: 17: Nucleotide sequence of lysE
SEQ ID NO: 18: Amino acid sequence encoded by lysE

What is claimed is:

1. A method for producing L-lysine comprising
   a) culturing a methanol-utilizing bacterium which requires L-methionine for its growth and has an ability to produce L-lysine in a medium containing methanol as a main carbon source
   b) allowing accumulation of L-lysine in a culture, and
   c) collecting the L-lysine from the culture.

2. The method according to claim 1, wherein said bacterium is a *Methylophilus* bacterium.

3. The method according to claim 2, wherein said *Methylophilus* bacterium is *Methylophilus methylotrophus*.

4. The method according to claim 1, wherein said *Methylophilus* bacterium is modified so that an enzymatic activity of dihydrodipicolinate synthase and an L-lysine secretion system are enhanced.

* * * * *

UNITED STATES PATENT AND TRADEMARK OFFICE
CERTIFICATE OF CORRECTION

| | |
|---|---|
| PATENT NO. | : 7,211,416 B2 |
| APPLICATION NO. | : 10/760283 |
| DATED | : May 1, 2007 |
| INVENTOR(S) | : Asahara et al. |

It is certified that error appears in the above-identified patent and that said Letters Patent is hereby corrected as shown below:

Delete Claim 4, and replace with the following: Col. 34, lines 43-46;

4. The method according to claim 1, wherein said methanol-utilizing bacterium is modified so that an enzymatic activity of dihydrodipicolinate synthase and an L-lysine secretion system are enhanced.

Signed and Sealed this

Seventh Day of August, 2007

JON W. DUDAS
*Director of the United States Patent and Trademark Office*

SEQUENCE LISTING

<160> NUMBER OF SEQ ID NOS: 18

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 1
agggaattcc ccgttctgga taatgttttt tgcgccgac                    39

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 2
cggatgcatc tagagttaac ctgcagggtg aaattgttat ccgctcacaa ttccacac    58

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 3
tgacctgcag gtttgcacag aggatggccc atgtt                        35

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 4
cattctagat ccctaaactt tacagcaaac cggcat                       36

<210> SEQ ID NO 5
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 5
catttcctgc aggcaaagga gatgagcgta atggtgatca tggaaatctt cattacaggt    60
ctgc                                                          64

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 6
gggcgagcta gaagagctcc aaaacccgcg aaaactaacc catcaacatc         50

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 7
tgagtgcaaa tttgacctca tcgtcagcaa                             30

<210> SEQ ID NO 8
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 8
ccagcctaca caatcgctca agacgtgtaa tgcaaggttt cataagcaag atggtattgt    60
ggca                                                               64

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: primer

<400> SEQUENCE: 9
ggctaattcc catgtcagcc gttaagtgtt gcagataacg ccttgcccgt caaatatgcc    60
gag                                                                63

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 10
acaggctgtt ccatgcctct gcagagggcg                             30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 11
gcattacacg tcttgagcga ttgtgtaggc                             30

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 12
ggaacactta acggctgaca tgggaattag cc                          32

<210> SEQ ID NO 13
<211> LENGTH: 30
<212> TYPE: DNA

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 13
atgacccaca cttgcaacaa ggcgatttgc                                    30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 14 gaagggttg ccttgtttga tgccactggc                                     30

<210> SEQ ID NO 15
<211> LENGTH: 4310
<212> TYPE: DNA
<213> ORGANISM: Methylophilus methylotrophus
<220> FEATURE:
<221> NAME/KEY: CDS
<222> LOCATION: (1236)..(2363)

<400> SEQUENCE: 15

```
tgagtgcaaa tttgacctca tcgtcagcaa cccgccttat atcgaaggca atgacccaca      60
cttgcaacaa ggcgatttgc gcttcgaacc tttatcagcc ctggcatccg gtgctgatgg     120
tctgcaagat atccgccaga tcattgccca ggcaccgcc tacttaaatg aaggggggctg     180 gttgatgctg aacatggtt acaaccaagc tccagcagtc caaaaattat tgaacgcaca     240
tggttttcaa gacatccaaa ccatcaagga tctgggcgat aatcctcgcg tcacccttgg     300
acaaataggc agcaccaacc cagtatgatt tttgcttgag taaagatacg ttagtctcaa     360
gtatcatttt ctggaaaaaa cattatgcaa tctatcccac atatcaaagc cgttttattt     420
gacctggatg gcgtgctcta catcggcaaa cagctgattc ccggcgcatt gtccgctgtg     480
gcacagttgc gcaaagcagg gattgccgtg cgctttgtca ccaataccag cacacttttcc    540 ctaaactcac tccagcaaaa gctgaacgac ctcggcttca atacggtgcc cgaagaaatc    600
atgagtgcac acaagcgac catccagtat ttaaaaaagc aatccaatcc ggtttgcaaa     660
ctattgctgg cagaggacgt taaaaaggac tttgcctgct ttgaccagtc tgcaaccgca    720
gccaattatg tggtgattgg tgatatcggt gaccagtggt cttatgagtt attgaatgaa    780
gtgtttcatt gcctggtgaa tggtgctcag ttaatcgcga ttcataaaaa ccgtttctgg    840
caaaccgaaa ctggcttgca aatggatatt ggtgcctttg ttaccggcct ggaatatgcc    900
agcaacaccc aggccatgct catgggtaaa ccttcccgcc atttttttcaa tcaggtggtg    960 gatacattac ggatgaagcc ttctgatatc gtgatggtgg gtgacgatat tgatgccgat   1020
gtgggtggcg cgcaggatgc tggactgcat ggcattctgg tgaaaccgg caagtaccgc   1080 gaaacctata cccgccttt agcgattgag ccagatgcga ttatccaatc cgtcgcagac   1140
cttcccacgt tgctgggttg tttatcgatt cagacccatt aaacgcaact tagcctgtct   1200
cgccgtttcg gcatgctgca tagtataatc gcggc atg tct gaa tcg aat tct       1253
                                    Met Ser Glu Ser Asn Ser
                                    1               5 gtt ggt atc gtt aaa gcg cag gtt gcg cac ttc acc cag ccg ctg acc      1301
Val Gly Ile Val Lys Ala Gln Val Ala His Phe Thr Gln Pro Leu Thr
            10                  15                  20
```

```
ctt aaa agc ggc gct gtg ttg cca caa tac cat ctt gct tat gaa acc        1349
Leu Lys Ser Gly Ala Val Leu Pro Gln Tyr His Leu Ala Tyr Glu Thr
        25                  30                  35 tat ggt gaa ctc aac gcg gcc aaa acc aat gcg gta ttg att tgt cac        1397
Tyr Gly Glu Leu Asn Ala Ala Lys Thr Asn Ala Val Leu Ile Cys His
 40                  45                  50 gcc ttg tcc ggc aat cat cat gtc gct ggt cgc tat tcg ccg gaa gat        1445
Ala Leu Ser Gly Asn His His Val Ala Gly Arg Tyr Ser Pro Glu Asp
 55                  60                  65                  70 aaa tat cct ggc tgg tgg gat aac ctt gtt ggc ccc ggt aag cca ctg        1493
Lys Tyr Pro Gly Trp Trp Asp Asn Leu Val Gly Pro Gly Lys Pro Leu
                 75                  80                  85 gat acc aac aag ttt ttt gtg att ggc ctc aac aat ctg ggc ggc tgt        1541
Asp Thr Asn Lys Phe Phe Val Ile Gly Leu Asn Asn Leu Gly Gly Cys
         90                  95                 100 cac ggt agt agc ggc cct tcc agc gta aat cca ctc act gac cgg cct        1589
His Gly Ser Ser Gly Pro Ser Ser Val Asn Pro Leu Thr Asp Arg Pro
                105                 110                 115 tac agt gca acg ttc cca gtc gtg acg gta gaa gac tgg gtg gaa tct        1637
Tyr Ser Ala Thr Phe Pro Val Val Thr Val Glu Asp Trp Val Glu Ser
120                 125                 130 cag gcg cgc ctg ttg gat tat ctt gga att gac caa ctg gca gcc gtg        1685
Gln Ala Arg Leu Leu Asp Tyr Leu Gly Ile Asp Gln Leu Ala Ala Val
135                 140                 145                 150 att ggt ggc agc ctg gga ggc atg caa gcg ctg cac tgg aat att gtc        1733
Ile Gly Gly Ser Leu Gly Gly Met Gln Ala Leu His Trp Asn Ile Val
                155                 160                 165 tac ccc gag cgt gta cgg cat gcc ttt gtc att gcc tct gcg ccc aac        1781
Tyr Pro Glu Arg Val Arg His Ala Phe Val Ile Ala Ser Ala Pro Asn
                170                 175                 180 ctg acc gca cag aac atg gcc ttt aac gaa gtg gca cgc cag gcg att        1829
Leu Thr Ala Gln Asn Met Ala Phe Asn Glu Val Ala Arg Gln Ala Ile
                185                 190                 195 att acc gac ccc gag ttt ttt gac ggc gat tat tat aat cat ggc acc        1877
Ile Thr Asp Pro Glu Phe Phe Asp Gly Asp Tyr Tyr Asn His Gly Thr
200                 205                 210 gtc ccc cgc cgc ggc ttg cgt att gcc cgt atg ctg ggg cat atc acc        1925
Val Pro Arg Arg Gly Leu Arg Ile Ala Arg Met Leu Gly His Ile Thr
215                 220                 225                 230 tac ttg tca gat gac gcc atg ggt gaa aaa ttt ggc cgc aaa ttg cgc        1973
Tyr Leu Ser Asp Asp Ala Met Gly Glu Lys Phe Gly Arg Lys Leu Arg
                235                 240                 245 cat ggc gat gtg aag tac agc ttt gat gtc gaa ttt gaa atg gaa tct        2021
His Gly Asp Val Lys Tyr Ser Phe Asp Val Glu Phe Glu Met Glu Ser
                250                 255                 260 tac ttg cgc tat cag ggc gac aag ttt gcc ggg gaa ttt gat gcc aac        2069
Tyr Leu Arg Tyr Gln Gly Asp Lys Phe Ala Gly Glu Phe Asp Ala Asn
                265                 270                 275 acc tat ttg cgc atg aca cgc gca ctg gac tat ttt gac ccg gcc ctc        2117
Thr Tyr Leu Arg Met Thr Arg Ala Leu Asp Tyr Phe Asp Pro Ala Leu
        280                 285                 290 gat tat gac ggc aat tta agc aag gcg ctc agc cgt gcc aag gcc aag        2165
Asp Tyr Asp Gly Asn Leu Ser Lys Ala Leu Ser Arg Ala Lys Ala Lys
295                 300                 305                 310 ttt gtc gtc atc tcg ttt acc act gac tgg cgc ttt tcg cct gcc cgc        2213
Phe Val Val Ile Ser Phe Thr Thr Asp Trp Arg Phe Ser Pro Ala Arg
                315                 320                 325 tca cgc gaa att gtc cag gcc ttg ctg gat aac gcc ttg ccc gtc aaa        2261
Ser Arg Glu Ile Val Gln Ala Leu Leu Asp Asn Ala Leu Pro Val Lys
                330                 335                 340
```

```
tat gcc gag gta act tct gcc cat ggc cat gac gct ttc ttg atg ccg    2309
Tyr Ala Glu Val Thr Ser Ala His Gly His Asp Ala Phe Leu Met Pro
        345                 350                 355 gat gcg cat tac cac gcc atc atg cgc gcc tac ctg gag caa atc aaa    2357
Asp Ala His Tyr His Ala Ile Met Arg Ala Tyr Leu Glu Gln Ile Lys
    360                 365                 370 gta tga cgaatgcaaa tattaccaat attcgcccag actttgcatt aattacaaac     2413
Val
375 tgggtgcaag caaaagccaa agtgctggat ctcggttgtg gcgatggcac actgctcacg   2473
catttacatg aaaccctgag caccaccggc tatggcatcg aaaaagatga tggtaactgg   2533
ctggcagcct taaaaaacgg ggtggacgtg attcaaatga accttgaaga aggcctgtcc   2593
ggctttgaag accagtcatt cgacacggtc atcctgtcgc agactttgca agccatgcac   2653
aatactgaga gcatcgtgca cgaaatgctg cgtgttggcc gcgaaatcat cgtgactttc   2713
cccaattttg gctattggcg caaccgcctg caaatcacgc tggggaatat gccggtctcc   2773
aaaagcctgc catatcaatg gtatgacacg cccaacgtgc atttatgcac catccacgac   2833
tttgaccact tttgccgcca gcacaacatt caagtcattg aacgtaaagt gattaccgat   2893
ggccaggata ttcattttt gcctaacctg ctgggcaatc tcgcaatgta ccggttgaaa    2953
cgcgccgcct aatcccgaca agagaccaaa gggtgccctt aagaaagatt gagcgctttc   3013
aggcgccggt aaagcgtatt tcggcttaac cccaactgac gggaaacggc cgaaatattg   3073
ccgccatgct gcagcatggc ctgccggatg gcttcatcgt ttttgggcttt caagttgccg   3133
gctgctaacg ctggccgtgc agaaccgacg ggtgtagaag gttcgctgat ggggtacatt   3193
tcatcgagaa agtcctgcat caaatgctgg cggccaatca cgccgccatc tgccaaggcc   3253
acggccgtgc gcaacacatt atgcaactgg cgtacattgc ccggccaagg atgcgcatta   3313
aacagtgcca tgacctcatc acttaagctg gcttgtggcg cctgttcgat ttgcagaatc   3373
acctgaatca gccttgccat atccagccgc tcgcgtagcg caggtaactg cacactcaag   3433
ccattgatgc ggtaatatag atcactgcga aactcgcccg ctgccacttt gtcttttaac   3493
ttctgattcg tcgcgctcag cagcataaag ttgaccggaa tcgccttgct gcctcccaac   3553
ggggtgacac tgcgctcttg cagcacgcgt aacaagcgtg cttgtagcga cagcggcata   3613
tcgccaatct catccaagaa caaggtgccg ccatccgctt gctgaatctt gccaatattg   3673
cctttgcgtt tcgccccggt gtacgcgccc tcctcatagc caaacagttc ggcttcaatc   3733
agcccttctg gcaaggccgc acagttgacg gcaataaacg gcttgttgcg gcgcgcactg   3793
gcgtcatgaa tggcacggga aaataattct ttacccgcgc cggtttcgcc gagaatcagc   3853
accggaatgt ccttatccag cacttgtttg acctgggtga tcgccaattt aaattggggg   3913
tcaccactat cgagcagctc caggctggcc gcagattcgc gtggcgtcat cgccactggc   3973
tttttggcga tagtggctgg ctggctggtc gatgcacgcg caaacaaacg ggcgccattg   4033
cgcagatgca agggaaatag gacatcagca tttaaaccgc gctgcttgaa cgaggcccat   4093
gactcgtcaa aaatgtcttc aaaagcaata cggcgcgcag acagactatc ctggtccagc   4153
ggcaaaccaa actggaactg gccgctacgg ttaatggcct gcaactggcc agtggcatca   4213
aacaaggcaa ccccttccca taaagtgcca ataaactctg ccgcacatg aaagtgcaca   4273
ccaatctcgc cctctgcaga ggcatggaac agcctgt                             4310
```

<210> SEQ ID NO 16

```
<211> LENGTH: 375
<212> TYPE: PRT
<213> ORGANISM: Methylophilus methylotrophus

<400> SEQUENCE: 16

Met Ser Glu Ser Asn Ser Val Gly Ile Val Lys Ala Gln Val Ala His
 1               5                  10                  15

Phe Thr Gln Pro Leu Thr Leu Lys Ser Gly Ala Val Leu Pro Gln Tyr
                20                  25                  30

His Leu Ala Tyr Glu Thr Tyr Gly Glu Leu Asn Ala Ala Lys Thr Asn
            35                  40                  45

Ala Val Leu Ile Cys His Ala Leu Ser Gly Asn His Val Ala Gly
        50                  55                  60

Arg Tyr Ser Pro Glu Asp Lys Tyr Pro Gly Trp Trp Asp Asn Leu Val
 65                  70                  75                  80

Gly Pro Gly Lys Pro Leu Asp Thr Asn Lys Phe Val Ile Gly Leu
                85                  90                  95

Asn Asn Leu Gly Gly Cys His Gly Ser Ser Gly Pro Ser Ser Val Asn
                100                 105                 110

Pro Leu Thr Asp Arg Pro Tyr Ser Ala Thr Phe Pro Val Val Thr Val
            115                 120                 125

Glu Asp Trp Val Glu Ser Gln Ala Arg Leu Leu Asp Tyr Leu Gly Ile
130                 135                 140

Asp Gln Leu Ala Ala Val Ile Gly Gly Ser Leu Gly Gly Met Gln Ala
145                 150                 155                 160

Leu His Trp Asn Ile Val Tyr Pro Glu Arg Val Arg His Ala Phe Val
                165                 170                 175

Ile Ala Ser Ala Pro Asn Leu Thr Ala Gln Asn Met Ala Phe Asn Glu
            180                 185                 190

Val Ala Arg Gln Ala Ile Ile Thr Asp Pro Glu Phe Phe Asp Gly Asp
        195                 200                 205

Tyr Tyr Asn His Gly Thr Val Pro Arg Arg Gly Leu Arg Ile Ala Arg
210                 215                 220

Met Leu Gly His Ile Thr Tyr Leu Ser Asp Asp Ala Met Gly Glu Lys
225                 230                 235                 240

Phe Gly Arg Lys Leu Arg His Gly Asp Val Lys Tyr Ser Phe Asp Val
                245                 250                 255

Glu Phe Glu Met Glu Ser Tyr Leu Arg Tyr Gln Gly Asp Lys Phe Ala
            260                 265                 270

Gly Glu Phe Asp Ala Asn Thr Tyr Leu Arg Met Thr Arg Ala Leu Asp
        275                 280                 285

Tyr Phe Asp Pro Ala Leu Asp Tyr Asp Gly Asn Leu Ser Lys Ala Leu
290                 295                 300

Ser Arg Ala Lys Ala Lys Phe Val Val Ile Ser Phe Thr Thr Asp Trp
305                 310                 315                 320

Arg Phe Ser Pro Ala Arg Ser Arg Glu Ile Val Gln Ala Leu Leu Asp
                325                 330                 335

Asn Ala Leu Pro Val Lys Tyr Ala Glu Val Thr Ser Ala His Gly His
            340                 345                 350

Asp Ala Phe Leu Met Pro Asp Ala His Tyr His Ala Ile Met Arg Ala
        355                 360                 365

Tyr Leu Glu Gln Ile Lys Val
370                 375
```

-continued

<210> SEQ ID NO 17
<211> LENGTH: 711
<212> TYPE: DNA
<213> ORGANISM: Brevibacterium lactofermentum
<220> FEATURE:
<221> NAME/KEY: CDS
<222> LOCATION: (1)..(711)

<400> SEQUENCE: 17

| | | | | | | | | | | | | | | | | |
|---|---|---|---|---|---|---|---|---|---|---|---|---|---|---|---|---|
| atg | gtg | atc | atg | gaa | atc | ttc | att | aca | ggt | ctg | ctt | ttg | ggg | gcc | agt | 48 |
| Met | Val | Ile | Met | Glu | Ile | Phe | Ile | Thr | Gly | Leu | Leu | Leu | Gly | Ala | Ser | |
| 1 | | | | 5 | | | | | 10 | | | | | 15 | | |
| ctt | tta | ctg | tcc | atc | gga | ccg | cag | aat | gta | ctg | gtg | att | aaa | caa | gga | 96 |
| Leu | Leu | Leu | Ser | Ile | Gly | Pro | Gln | Asn | Val | Leu | Val | Ile | Lys | Gln | Gly | |
| | | | 20 | | | | | 25 | | | | | 30 | | | |
| att | aag | cgc | gaa | gga | ctc | att | gcg | gtt | ctt | ctc | gtg | tgt | tta | att | tct | 144 |
| Ile | Lys | Arg | Glu | Gly | Leu | Ile | Ala | Val | Leu | Leu | Val | Cys | Leu | Ile | Ser | |
| | | 35 | | | | | 40 | | | | | 45 | | | | |
| gac | gtc | ttt | ttg | ttc | atc | gcc | ggc | acc | ttg | ggc | gtt | gat | ctt | ttg | tcc | 192 |
| Asp | Val | Phe | Leu | Phe | Ile | Ala | Gly | Thr | Leu | Gly | Val | Asp | Leu | Leu | Ser | |
| | 50 | | | | | 55 | | | | | 60 | | | | | |
| aat | gcc | gcg | ccg | atc | gtg | ctc | gat | att | atg | cgc | tgg | ggt | ggc | atc | gct | 240 |
| Asn | Ala | Ala | Pro | Ile | Val | Leu | Asp | Ile | Met | Arg | Trp | Gly | Gly | Ile | Ala | |
| 65 | | | | | 70 | | | | | 75 | | | | | 80 | |
| tac | ctg | tta | tgg | ttt | gcc | gtc | atg | gca | gcg | aaa | gac | gcc | atg | aca | aac | 288 |
| Tyr | Leu | Leu | Trp | Phe | Ala | Val | Met | Ala | Ala | Lys | Asp | Ala | Met | Thr | Asn | |
| | | | | 85 | | | | | 90 | | | | | 95 | | |
| aag | gtg | gaa | gcg | cca | cag | atc | att | gaa | gaa | aca | gaa | cca | acc | gtg | ccc | 336 |
| Lys | Val | Glu | Ala | Pro | Gln | Ile | Ile | Glu | Glu | Thr | Glu | Pro | Thr | Val | Pro | |
| | | | 100 | | | | | 105 | | | | | 110 | | | |
| gat | gac | acg | cct | ttg | ggc | ggt | tcg | gcg | gtg | gcc | act | gac | acg | cgc | aac | 384 |
| Asp | Asp | Thr | Pro | Leu | Gly | Gly | Ser | Ala | Val | Ala | Thr | Asp | Thr | Arg | Asn | |
| | | 115 | | | | | 120 | | | | | 125 | | | | |
| cgg | gtg | cgg | gtg | gag | gtg | agc | gtc | gat | aag | cag | cgg | gtt | tgg | gta | aag | 432 |
| Arg | Val | Arg | Val | Glu | Val | Ser | Val | Asp | Lys | Gln | Arg | Val | Trp | Val | Lys | |
| | 130 | | | | | 135 | | | | | 140 | | | | | |
| ccc | atg | ttg | atg | gca | atc | gtg | ctg | acc | tgg | ttg | aac | ccg | aat | gcg | tat | 480 |
| Pro | Met | Leu | Met | Ala | Ile | Val | Leu | Thr | Trp | Leu | Asn | Pro | Asn | Ala | Tyr | |
| 145 | | | | | 150 | | | | | 155 | | | | | 160 | |
| ttg | gac | gcg | ttt | gtg | ttt | atc | ggc | ggc | gtc | ggc | gcg | caa | tac | ggc | gac | 528 |
| Leu | Asp | Ala | Phe | Val | Phe | Ile | Gly | Gly | Val | Gly | Ala | Gln | Tyr | Gly | Asp | |
| | | | | 165 | | | | | 170 | | | | | 175 | | |
| acc | gga | cgg | tgg | att | ttc | gcc | gct | ggc | gcg | ttc | gcg | gca | agc | ctg | atc | 576 |
| Thr | Gly | Arg | Trp | Ile | Phe | Ala | Ala | Gly | Ala | Phe | Ala | Ala | Ser | Leu | Ile | |
| | | | 180 | | | | | 185 | | | | | 190 | | | |
| tgg | ttc | ccg | ctg | gtg | ggt | ttc | ggc | gca | gca | gca | ttg | tca | cgc | ccg | ctg | 624 |
| Trp | Phe | Pro | Leu | Val | Gly | Phe | Gly | Ala | Ala | Ala | Leu | Ser | Arg | Pro | Leu | |
| | | 195 | | | | | 200 | | | | | 205 | | | | |
| tcc | agc | ccc | aag | gtg | tgg | cgc | tgg | atc | aac | gtc | gtc | gtg | gca | gtt | gtg | 672 |
| Ser | Ser | Pro | Lys | Val | Trp | Arg | Trp | Ile | Asn | Val | Val | Val | Ala | Val | Val | |
| | 210 | | | | | 215 | | | | | 220 | | | | | |
| atg | acc | gca | ttg | gcc | atc | aaa | ctg | atg | ttg | atg | ggt | tag | | | | 711 |
| Met | Thr | Ala | Leu | Ala | Ile | Lys | Leu | Met | Leu | Met | Gly | | | | | |
| 225 | | | | | 230 | | | | | 235 | | | | | | |

<210> SEQ ID NO 18
<211> LENGTH: 236
<212> TYPE: PRT
<213> ORGANISM: Brevibacterium lactofermentum

<400> SEQUENCE: 18

Met Val Ile Met Glu Ile Phe Ile Thr Gly Leu Leu Leu Gly Ala Ser

-continued

```
  1               5                  10                 15
Leu Leu Leu Ser Ile Gly Pro Gln Asn Val Leu Val Ile Lys Gln Gly
             20                 25                 30

Ile Lys Arg Glu Gly Leu Ile Ala Val Leu Leu Val Cys Leu Ile Ser
         35                 40                 45

Asp Val Phe Leu Phe Ile Ala Gly Thr Leu Gly Val Asp Leu Leu Ser
     50                 55                 60

Asn Ala Ala Pro Ile Val Leu Asp Ile Met Arg Trp Gly Gly Ile Ala
 65                 70                 75                 80

Tyr Leu Leu Trp Phe Ala Val Met Ala Ala Lys Asp Ala Met Thr Asn
             85                 90                 95

Lys Val Glu Ala Pro Gln Ile Ile Glu Glu Thr Glu Pro Thr Val Pro
            100                105                110

Asp Asp Thr Pro Leu Gly Gly Ser Ala Val Ala Thr Asp Thr Arg Asn
            115                120                125

Arg Val Arg Val Glu Val Ser Val Asp Lys Gln Arg Val Trp Val Lys
        130                135                140

Pro Met Leu Met Ala Ile Val Leu Thr Trp Leu Asn Pro Asn Ala Tyr
145                150                155                160

Leu Asp Ala Phe Val Phe Ile Gly Gly Val Gly Ala Gln Tyr Gly Asp
            165                170                175

Thr Gly Arg Trp Ile Phe Ala Ala Gly Ala Phe Ala Ala Ser Leu Ile
            180                185                190

Trp Phe Pro Leu Val Gly Phe Gly Ala Ala Ala Leu Ser Arg Pro Leu
            195                200                205

Ser Ser Pro Lys Val Trp Arg Trp Ile Asn Val Val Val Ala Val Val
    210                215                220

Met Thr Ala Leu Ala Ile Lys Leu Met Leu Met Gly
225                230                235
```